United States Patent [19]

Burd et al.

[11] Patent Number: 5,457,053
[45] Date of Patent: Oct. 10, 1995

[54] REAGENT CONTAINER FOR ANALYTICAL ROTOR

[75] Inventors: Tammy L. Burd, Fremont; Carol T. Schembri, San Mateo, both of Calif.

[73] Assignee: Abaxis, Inc., Sunnyvale, Calif.

[21] Appl. No.: 226,924

[22] Filed: Apr. 13, 1994

Related U.S. Application Data

[62] Division of Ser. No. 833,689, Feb. 11, 1992, Pat. No. 5,304,348.

[51] Int. Cl.[6] ................................ G01N 9/30; B04B 7/00
[52] U.S. Cl. ................................................ 436/45; 422/72
[58] Field of Search .............................. 436/45; 422/64, 422/72, 102; 494/31, 45; 222/81, 83, 167, 541

[56] References Cited

U.S. PATENT DOCUMENTS

| 4,266,681 | 5/1981 | Fredericks | 215/32 |
| 4,390,499 | 6/1983 | Curtis et al. | 422/72 |
| 5,162,237 | 11/1992 | Messenger | 436/523 |

*Primary Examiner*—Robert J. Warden
*Assistant Examiner*—Robert Carpenter
*Attorney, Agent, or Firm*—Townsend and Townsend and Crew

[57] ABSTRACT

An analytical rotor which comprises a receptacle for receiving a post on a centrifuge and means in the rotor body proximate to the receptacle for releasing a liquid in response to mounting the rotor in the centrifuge is disclosed. The means for releasing the liquid is preferably a sealed container shiftably positioned in a chamber proximate the receptacle.

5 Claims, 4 Drawing Sheets

5,457,053

REAGENT CONTAINER FOR ANALYTICAL ROTOR

This is a Division of application Ser. No. 07/833,689, filed Feb. 11, 1992, now U.S. Pat. No. 5,304,348.

BACKGROUND OF THE INVENTION

1. Field of the Invention

The present invention relates generally to devices and methods for optically analyzing biological fluids. In particular, it relates to the design and use of centrifugal rotors which allow release of a predetermined volume of a fluid in response to mounting the rotor in a centrifuge.

Blood plasma and other biological tests frequently require that predetermined volumes of liquids be quickly and completely mixed with a biological fluid for analysis in a variety of optical tests or assays. It is also desirable to separate potentially-interfering cellular components of the material from the biological fluid prior to testing. Such mixing and separation steps have heretofore been typically performed by centrifugation to separate, for instance, blood plasma from the cellular components, followed by manual or automated pipetting of predetermined volumes of the blood plasma into separate test wells for optical analysis. Such procedures are labor-intensive and time-consuming, and various automated systems and methods have been proposed for providing multiple aliquots of plasma suitable for testing in a more efficient manner.

Prior art rotors have frequently utilized complex designs which are difficult and costly to manufacture. Often, the rotors require various separable parts or components which are brought together or separated at different points in the centrifugation procedure. Previous centrifugal rotors have often been limited in the number of discrete samples and test wells which they can provide, and in some cases require the use of a separate displacement fluid to effect flow of blood and plasma through the system.

For these reasons, it would be desirable to provide improved centrifugal rotors and methods suitable for quickly and easily delivering a predetermined volume of liquid to a receiving chamber in the rotor. The methods should be simple and be capable of being performed in relatively short times. In particular, the methods should require relatively few steps and should be capable of being performed with little or no intervention or manipulation by the operator.

2. Description of the Background Art

U.S. Pat. No. 4,999,304 discloses a centrifuge for separating constituents of fluids comprising a separate diluent chamber. U.S. Pat. No. 4,963,498 discloses devices which rely upon capillaries, chambers, and orifices to pump and mix fluids for optical analysis. U.S. Pat. No. 4,898,832 discloses an analytical rotor comprising a series of reagent chambers. U.S. Pat. No. 4,814,144 discloses a centrifugal rotor into which various reagents may be introduced. U.S. Pat. No. 4,756,883 relates to a centrifugal rotor comprising various reagents in a dry tabletized form. U.S. Pat. No. 4,743,558 is directed to a rotor having a plurality of storage chambers for liquid reagents. U.S. Pat. No. 4,412,973 discloses a rotor comprising a reagent container having an outwardly disposed tip. The tip is broken off and the container is opened by tilting the container. U.S. Pat. No. 4,387,164 discloses a rotor having a reagent contained within a carrier solid organic binder which is fixed within the rotor. European Patent Application No. 8,105,106.0 discloses a reagent container which is opened as the result of centrifugal force.

SUMMARY OF THE INVENTION

The present invention is an analytical rotor which comprises a receptacle for receiving a post on a centrifuge and means in the rotor body proximate to the receptacle for releasing a liquid in response to mounting the rotor in the centrifuge. The means for releasing the liquid is preferably a sealed container shiftably positioned in a chamber proximate the receptacle.

The sealed container may comprise one or compartments. If more than one compartment is present, each compartment may comprise the same or different liquid.

In one embodiment, the container is sealed with a laminated foil seal having a tab anchored to the rotor. Preferably, the foil seal is folded back on itself over the top of the container so that the foil seal is peeled from the container in response to the insertion of the post in the receptacle.

In an alternative embodiment, the container comprises a foil seal and a rigid side having a scribe mark. The ends of the container are secured to the rotor such that the container opens along the scribe mark in response to the insertion of the post in the receptacle. The rigid side is preferably formed from sheet plastic material.

The receptacle which accepts the post is typically positioned on the bottom of the rotor at the axis of rotation. The post may be positioned on the centrifuge spindle or the post may be the spindle itself. In certain embodiments, the post may indirectly shift the container by engaging a piston which then shifts the container.

The rotor is preferably used for the analysis of a biological sample, such as whole blood. The rotor will thus comprise a means for introducing the sample into the rotor body. The liquid in the container is preferably a reagent used in the analysis of blood, typically, a diluent suitable for diluting whole blood prior to analysis.

The rotor preferably comprises a receiving chamber for accepting the fluid released from container. If the container comprises more than one compartment, each compartment may be connected to a separate receiving chamber. The receiving chamber is typically a mixing chamber in which the liquid, e.g. diluent, is mixed with a marker compound. The rotor will preferably comprise appropriate chambers and passages for mixing the diluent with the biological sample, separating cellular material, and performing various optical analyses of the sample.

DESCRIPTION OF THE PREFERRED EMBODIMENT

Figure 1:
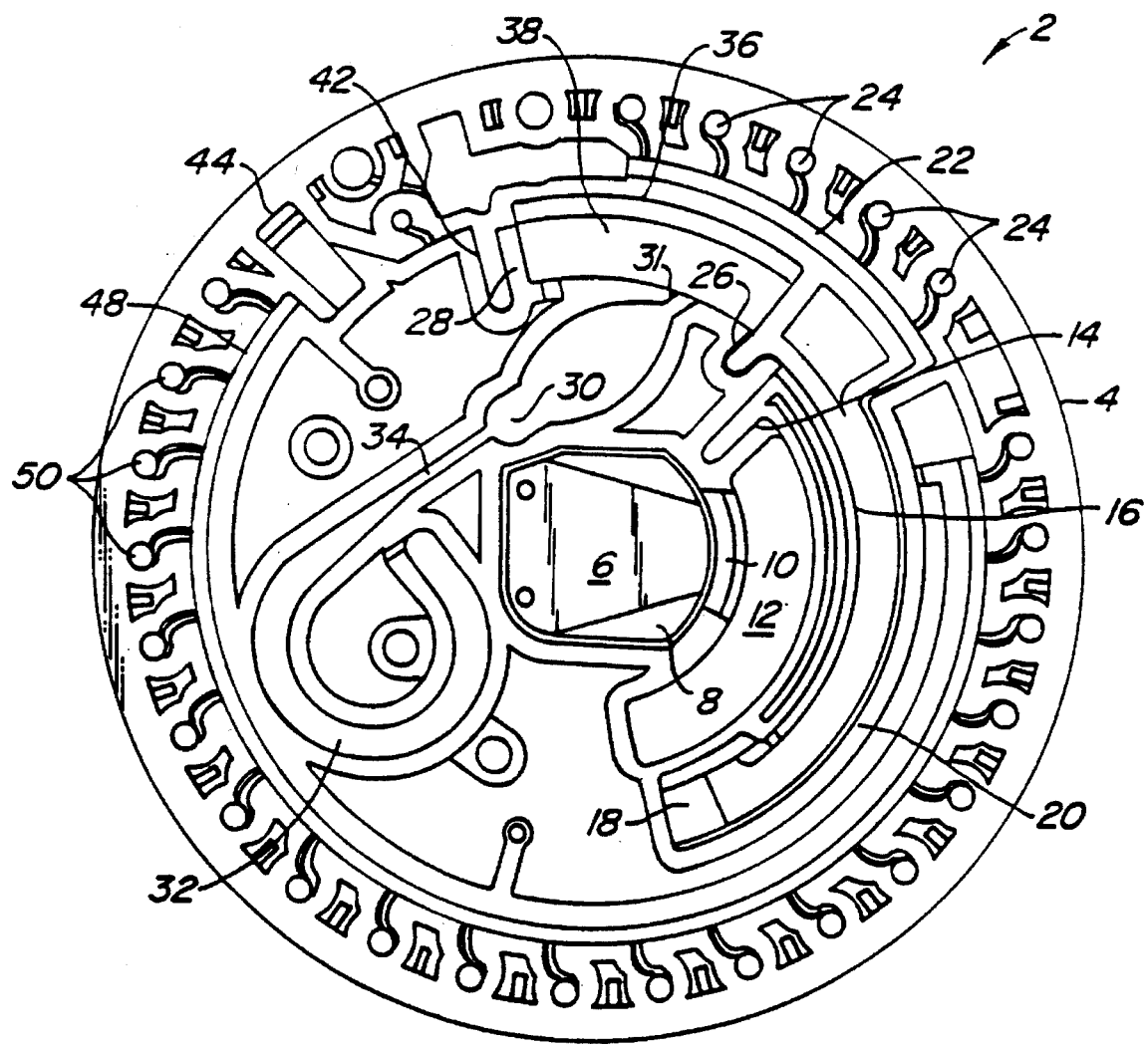
FIG. 1 is a top plan view of the bottom layer of a rotor of the present invention showing the position of the reagent container in relation to various passages and chambers in the rotor.

The present invention provides devices and methods for automatically releasing a predetermined volume of liquid in a centrifugal rotor. This is preferably carried out using a sealed reagent container which is shifted to an open position in response to the insertion of a post into a receptacle in the rotor. The contents are then removed from the container and delivered to a receiving chamber by centrifugal force or gravity. The receiving chamber can have a variety of functions. For instance, it can be a mixing chamber, a measuring chamber, or a separation chamber. The receiving chamber is preferably a separation chamber, where cellular material in the biological sample is removed.

The sealed reagent container of the present invention is preferably formed of a material which will provide an excellent water and water vapor transmission barrier. Various plastics and other polymeric materials such as high density polyethylene are typically used. The container may be manufactured by a number of techniques including molding, pressure or vacuum forming, and machining.

The container can be formed to comprise a single compartment or more than one compartment. The liquid in the compartments may be delivered to the same receiving chamber or each may be connected to separate receiving chambers. Each compartment may contain the same or a different reagent. For instance, two compartments can be connected to a mixing chamber in which two liquids (e.g., a diluent and a marker compound) are mixed before delivery to another chamber.

The container is typically sealed with foil. The foil seal is preferably laminated with polyethylene or another plastic and die cut to the appropriate shape to cover the opening. If the container comprises more than one compartment, each compartment may have a separate foil seal, or a single foil seal may be used for the entire container. The assembly is formed by filling the container with the specified volume of reagent and heat sealing or ultrasonically welding the foil onto the container.

The sealed reagent container is usually positioned in a chamber which has sufficient size to allow the container to be shifted to an open position. The container is positioned adjacent to a receptacle which can be any shape or size as long as the container cannot pass through. The container is secured in the rotor and its contents are isolated from the rest of the rotor until the analytical rotor is used.

The receptacle is typically on the bottom surface of the rotor and the sealed container is opened when the rotor is mounted on a spindle in a centrifuge. The spindle itself may shift the container or the spindle may include a post which enters the receptacle. When the rotor is placed on the spindle, the post shifts the container and creates an opening in the container. Alternatively, a mechanical arm or solenoid shifts the container. Thus, the opening of the container may be delayed until a predetermined time in the testing cycle. In this embodiment, the container may be positioned away from the center of the rotor and the post need not be positioned on the spindle. Additionally, the receptacle may be on a surface other than the bottom surface of the rotor and the container can be moved sideways or down.

In one embodiment, the container is sealed with a laminated foil seal having a tab which is secured to the rotor body. Various methods of securing the tab include clamping it between layers in the rotor, welding, and gluing. A simple method is achieved by punching one or more holes in the foil tab and capturing the tab on posts in the rotor. This is a convenient method to register the foil before the rotor is sealed, typically by ultrasonic welding.

When the rotor is placed on the spindle, the post pushes up on the bottom of the container causing it to travel vertically while the foil remains secured. The foil seal is folded back on itself such that foil peels back from the side of the container opposite the secured tab and creates an opening as the container is shifted upward. In this design, the container preferably has a slanting side on the wall of the container where the opening is formed to facilitate the complete emptying of the container. Emptying of the container may be further facilitated by including a recess in the cover of the rotor.

Additional designs for automatically opening and emptying a container in the rotor can also be used. For instance, a form, fill and seal container with a scribe mark on the rigid side of the container can be used. The container is typically formed from a sheet plastic material, typically by vacuum or pressure forming. The container is filled with the appropriate reagent and sealed with foil. The container is mounted into the rotor by securing the ends of the container, typically by capturing them in grooves or behind posts. When the rotor is mounted in the centrifuge, the spindle or a post extends into the chamber and pushes the center portion of the container radially outward. The pressure of the spindle or post causes the container to snap at the scribe mark, opening the container. As with the previous embodiment, the contents may now be moved by centrifugal forces or gravity to the location desired.

The analytical rotors of the present invention are capable of being mounted on a conventional laboratory centrifuge of the type commercially available from suppliers, such as Beckman Instruments, Inc., Spinco Division, Fullerton, Calif.; Fisher Scientific, Pittsburgh, Pa.; VWR Scientific, San Francisco, Calif., and the like. Generally, the rotors will include a receptacle or other coupling device suitable for mounting on a vertical drive shaft or spindle within the centrifuge. This receptacle may or may not be the same as the receptacle positioned below the sealed reagent container. The particular design of the receptacle or coupling device will depend on the nature of the centrifuge, and it will be appreciated that the centrifugal rotor of the present invention may be adapted to be used with most types of centrifuges which are now available or which may become available in the future so long as the velocity profile can be programmed.

The analytical rotors comprise a body structure which maintains a desired geometric pattern or relationship between a plurality of chambers and interconnecting inlet channels, as described in more detail below. Usually, the body will be a substantially solid plate with the chambers and passages formed as spaces or voids in an otherwise solid matrix. Conveniently, such solid plate structures may be formed by laminating a plurality of separately formed layers together into a composite structure where the chambers and passages are generally formed between adjacent layers. The individual layers may be formed by injection molding, machining, and combinations thereof, and will usually be joined together, typically using a suitable adhesive or by ultrasonic welding. The final enclosed volumes are formed when the layers are brought together. Of course, the analytical rotor could also be formed as a plurality of discrete components, such as tubes, vessels, chambers, etc., arranged in a suitable structural framework. Such assemblies, however, are generally more difficult to manufacture and are therefore less desirable than those formed in a substantially solid plate.

The analytical rotors may be formed from a wide variety of materials and may optionally include two or more materials. Usually, the materials will be transparent, for example clear plastic, so that the presence and distribution of biological sample, and various reagents, may be observed within the various internal chambers and passages. Also, it is generally required that the test wells or cuvettes formed within the rotor have suitable optical paths formed therethrough so that the contents of the test well may be observed spectrophotometrically, fluorometrically, or by other visual assessment techniques. In the exemplary embodiment described below, the rotor is formed from acrylic resins having the required optical properties, at least in those areas which define the optical paths.

The apparatus of the invention is very easy to manufacture and can be produced at a very low cost, making the rotor suitable for use as a disposable in testing a number of biological samples such as whole blood. The apparatus can provide for automatic combination of blood with a predetermined volume of reagent or diluent and can apportion substantially equal volumes of blood or plasma among the plurality of cuvettes. More importantly, the apparatus is suitable for use with a variety of conventional analytic measurement devices, such as spectrophotometers and fluorometers, which allow the plasma in the cuvettes to be individually examined without the need to remove the plasma.

Although the present invention is particularly suitable for analyzing whole blood or blood plasma, it will be useful with a wide variety of other biological fluids, such as urine, sputum, semen, saliva, ocular lens fluid, cerebral fluid, spinal fluid, amniotic fluid, and tissue culture media, as well as food and industrial chemicals, and the like. The rotors of the invention also provide for separation of cellular material, accurate measurement of volumes of sample, distribution of the sample into a plurality of test wells or cuvettes, and rapid optical analyses of the sample. All of the above steps preferably occur without having to transfer aliquots of the plasma from the apparatus and as a result of centrifugal force generated by the spinning rotor.

Where it may be desirable to separate cells and other interfering substances prior to analysis or assay, the devices and methods described in U.S. Pat. No. 5,061,381, which is incorporated herein by reference) are preferably used. That application discloses a centrifugal rotor for separating plasma from whole blood which includes a separation chamber comprising a radially-outward cell trap and a radially-inward receptacle region separated from the cell trap by a capillary region. Spinning of the rotor causes the cellular components of the whole blood to enter the cell trap, while the separated plasma flows back into the receptacle region. The capillary region prevents the separated cellular components from flowing back into the receptacle region with the plasma.

Measurement and delivery of predetermined volumes of reagents and biological sample is preferably accomplished as described in U.S. Pat. No. 5,173,193, which is incorporated herein by reference. The application discloses and claims a rotor comprising a bulk fluid chamber containing a bulk amount of fluid and a metering chamber which has a predetermined volume. The bulk fluid flowing into the metering chamber having a predetermined volume and excess fluid flows out into an overflow chamber. The fluid in the metering chamber is delivered to the receiving chamber through an exit duct which preferably prevents flow of fluid until after the metering chamber is filled.

The distribution of fluid to cuvettes or test wells is preferably accomplished using the methods and devices disclosed in U.S. Pat. No. 5,122,284 which is incorporated herein by reference. In that application, a centrifugal rotor comprising a plurality of generally radial inlet channels connects each cuvette to a collection chamber. Each inlet channel has a discrete flow path for fluid to enter the cuvette and another discrete flow path for gas to exit the cuvette as the cuvette is filled. As the rotor is spun, fluid enters the cuvettes from the collection chamber through the inlet channels, which also allow gas in the cuvettes to escape, thus avoiding the creation of bubbles in the cuvette as the cuvettes are filled. In some embodiments, a reflective surface is positioned radially inward from each cuvette. The reflective surface is oriented such that a generally horizontal light beam is deflected in a generally vertical direction and vice versa.

The apparatus and method of the present invention are suitable for performing a wide variety of analytic procedures which are beneficially or necessarily performed on biological samples, preferably blood plasma. The analytic procedures will generally require that the blood plasma be combined with one or more reagents so that some optically detectable change occurs in the plasma which may be related to measurement of a particular component or characteristic of the plasma. Preferably, the plasma will undergo a reaction or other change which results in a change in color, fluorescence, luminescence, or the like, which may be measured by conventional spectrophotometers, fluorometers, light detectors, etc. In some cases, immunoassays and other specific binding assays may be performed in the test wells. Generally, however, such assay procedures must be homogeneous and not require a separation step. In other cases, it will be possible to accommodate heterogeneous assay systems by providing a means to separate blood plasma from the test wells after an immunological reaction step has occurred.

Conventional blood assays which may be performed include glucose, lactate dehydrogenase, serum glutamic-oxaloacetic transaminase (SGPT), serum glutamic-pyruvic transaminase (SGPT), blood urea (nitrogen) (BUN), total protein, alkalinity, phosphatase, bilirubin, calcium, chloride, sodium, potassium, magnesium, and the like. This list is not exhaustive and is intended merely to exemplify the assays which may be performed using the apparatus and method of the present invention. Usually, these tests will require that the blood plasma be combined with one or more reagents which results in an optionally detectable, usually photometrically detectable, change in the plasma. The required reagents are well known and amply described in the patent and scientific literature. Production of lyophilized reagent spheres suitable for use in the present invention is described in copending application U.S. Ser. No. 07/747,179, which is incorporated herein by reference.

Referring now to FIGS. 1–5, centrifugal rotors constructed in accordance with the principles of the present invention will be described in detail. The flow of liquid through the various passages and chambers described below occurs as a result of centrifugal forces generated by the spinning rotor. The siphons used to transfer fluids between chambers operate as described in U.S. Pat. No. 5,173,193, supra. Briefly, each siphon has an elbow substantially the same distance from the center of the rotor as the radially most inward point of the chamber holding the fluid. As the rotor is spinning the fluid does not flow past the elbow. The rotor is then stopped, which allows capillary forces to "prime" the siphon by pulling fluid just around the elbow. When the rotor is restarted, the combined centrifugal and capillary forces draw the remaining fluid out of the chamber into the next chamber.

The rotor body 2 of the present invention is in the form of a substantially solid disc, the bottom layer 4 of which is shown in FIG. 1. A sealed reagent container 6 is positioned in a chamber 8 in the bottom layer 4, and is radially inward from an outlet channel 10 which empties into a mixing chamber 12. The reagent container typically contains a diluent to be mixed with a biological sample. Various diluents known to those skilled in the art are suitable for use in the present invention. For instance, if the sample is blood, standard diluents such as normal saline solution (0.5% NaCl in water), phosphate buffered solution, Ringer's lactate solution, and the like may be used.

The sealed reagent container 6 is typically opened in response to mounting the rotor body 2 in a centrifuge. The mechanism by which the reagent container 6 is opened is described in detail below. After opening, the reagent in the reagent container flows through the outlet channel 10 to the mixing chamber 12. The mixing chamber 12 will typically comprise a photometrically detectable marker compound for determining the dilution of the biological sample being tested. Suitable marker compounds are disclosed in copending application U.S. Ser. No. 07/747,179, supra. Such compounds include dyes such as 1,1',3,3,3',3'-hexamethylindotricarbocyanine iodide, 1,1'-bis(sulfoalkyl)- 3,3,3',3'-tetramethylindotricarbocyanine salts, enzyme substrates (such as lactate and p-nitrophenylphosphate) and enzymes (such as D-lactate dehydrogenase and microbial glucose-6-phosphate dehydrogenase).

After mixing, the diluent exits the mixing chamber 12 through siphon 14 and enters the metering chamber 16. The metering chamber 16 is connected to an overflow chamber 18. Measurement of the diluent in the metering chamber 16 is as described in U.S. Pat. No. 5,173,193, supra. To provide the predetermined volume of diluent, the volume of the metering chamber 16 must be less than that of the reagent container. Excess diluent flows into the overflow chamber 18, leaving the predetermined volume of diluent in the metering chamber.

The excess diluent in the overflow chamber 18 exits via passage 20 and enters collection chamber 22. The diluent then flows radially outward to system cuvettes 24 for use as a reference in the optical analysis of the biological sample, described below.

The predetermined volume of diluent in the metering chamber 16 exits through siphon 26 and enters the separation chamber 28, where it mixes with and dilutes the biological sample to be analyzed. The sample is applied to the rotor body 2 through an application port in the top layer (not shown). The sample metering chamber 30 is connected to a sample overflow chamber 32 by a connecting passage 34. The depth of the sample metering chamber 30 and overflow chamber 32 will typically be selected to provide for capillary dimensions. The measured volume of sample then enters the separation chamber 28 through passage 29.

The separation chamber 28 is used to remove cellular material from a biological sample, such as whole blood. The separation chamber 28 includes a cell trap 36 formed at its radially-outward periphery and a receptacle region 38 formed along its radially-inward perimeter. A capillary region 40 is formed between the receptacle region 38 and the cell trap 36 in order to inhibit the backflow of cellular material after it has entered the cell trap 36 as a result of centrifugal separation. The receptacle region 38 has a volume which is capable of receiving the diluted cell-free blood plasma.

The diluted plasma exits the separation chamber 28 through siphon 42 and enters a second separation chamber 44 where further separation of cellular material is carried out. The diluted sample then exits through passage 46 and enters the collection chamber 48 where it is delivered to cuvettes 50 for optical analysis. The cuvettes 50 contain reagents necessary for the optical analysis of the sample, typically in the form of lyophilized reagent spheres as described in U.S. Ser. No. 07/747,179, supra.

Figure 2A:
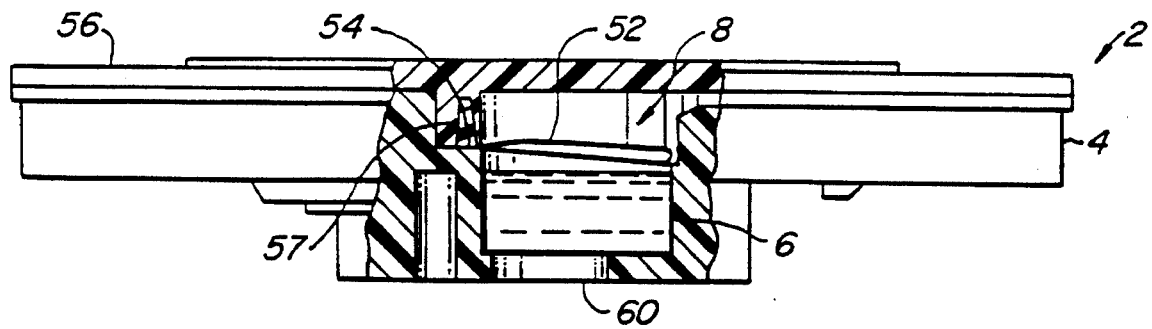
FIG. 2A is side view of the rotor showing the position of the reagent container before the post is inserted into the rotor.
Figure 2B:
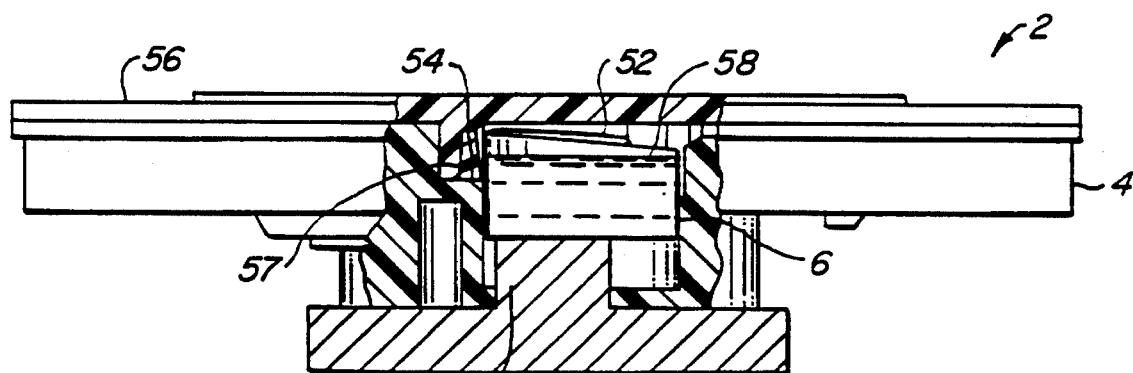
FIG. 2B is side view of the rotor showing the position of the reagent container after the post is inserted into the rotor.

The opening of the sealed reagent container 6 is shown in detail in FIGS. 2A and 2B. FIG. 2A shows the position of the reagent container 6 before the rotor body 2 is placed in the centrifuge. Here, it can be seen that a reagent container 6 is positioned at the bottom of chamber 8. The container is sealed with a laminated foil seal 52 which comprises a tab 54 which is clamped between the bottom layer 4 and the top layer 56 by means of securing post 57 and holes in the tab 54 (not shown). FIG. 2A shows the position of the reagent container 6 in the chamber 8 after the rotor body 2 is placed on the centrifuge and a post 58 has entered through receptacle 60. As discussed above, the post 58 is typically the spindle of the centrifuge. The post 58 shifts the reagent container 6 upward. This motion causes the foil seal 52 to be pulled back from the top of the reagent container 6, because the foil seal 52 is secured to the rotor 2 at tab 54. An opening 55 is created and the diluent in the reagent container then exits through outlet channel 10.

Figure 3A:
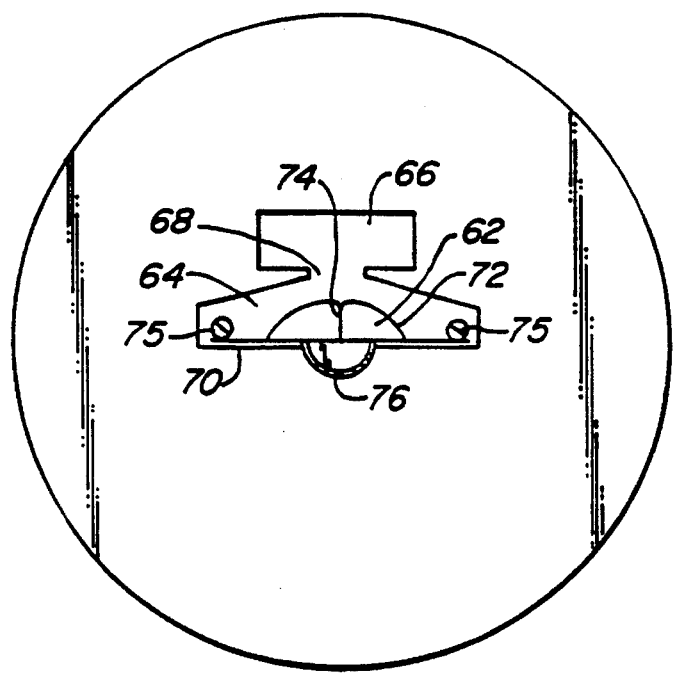
FIG. 3A is a top plan view of the bottom layer of a rotor comprising an alternate embodiment of the reagent container showing the position of the container before the post is inserted into the rotor.
Figure 3B:
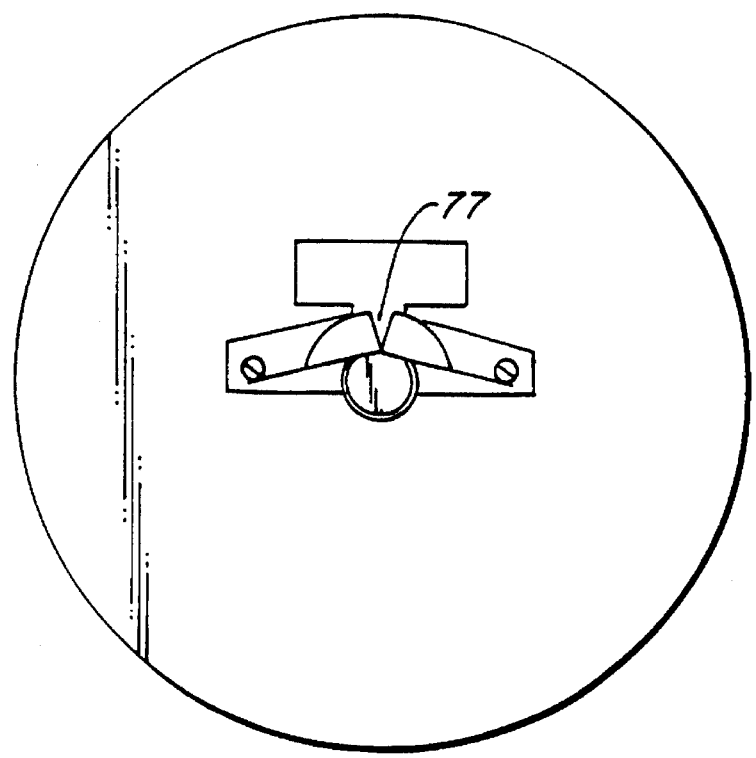
FIG. 3B is a top plan view of the bottom layer of a rotor comprising an alternate embodiment of the reagent container showing the position of the container after the post is inserted into the rotor.

An alternative embodiment is presented in FIGS. 3A and 3B. In this embodiment the reagent container 62 is positioned in a chamber 64 which empties into a receiving chamber 66 through outlet channel 68. Preferably, the receiving chamber 66 will be a mixing chamber which empties into the series of chambers and passages shown in FIG. 1. The reagent container 62 comprises a foil seal 70 and a rigid side 72 having a scribe mark 74. The container 62 is held in place by restraining posts 75.

FIG. 3B shows the position of the reagent container 62 after the spindle or post 76 has extended through receptacle 78 and into the chamber 64. In this position, the post 76 has shifted reagent container 62 toward the receiving chamber 66 causing the rigid side 72 to split along the scribe mark 74 and creating opening 77. Fluid then enters the receiving chamber 66 in response to the spinning of the rotor.

Figure 4A:
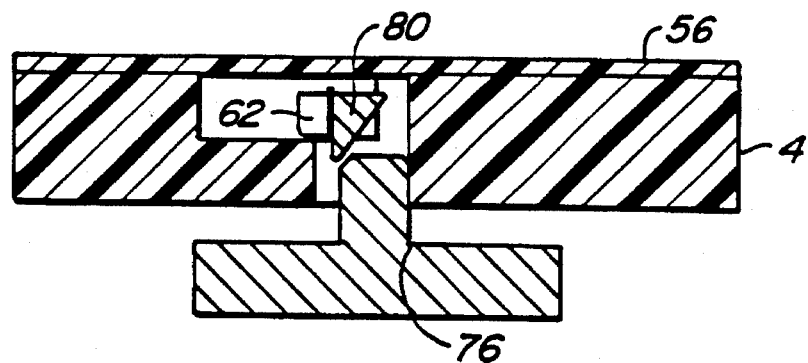
FIG. 4A is a side view of a rotor comprising a piston which shifts the reagent container showing the positions of the piston and reagent container before the piston is engaged by the post.
Figure 4B:
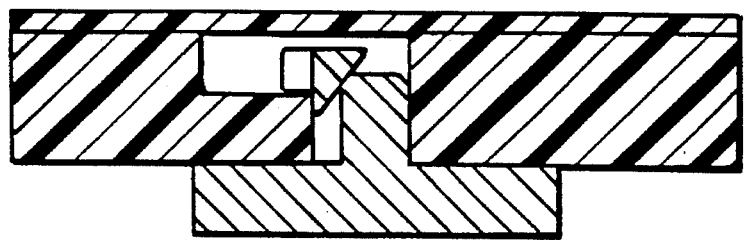
FIG. 4B is a side view of a rotor comprising a piston which shifts the reagent container showing the positions of the piston and reagent container after the piston is engaged by the post.

FIGS. 4A and 4B show an alternate embodiment in which the post 76 indirectly shifts the reagent container 62 through movement of a piston 80. FIG. 4A shows the reagent container 62 positioned in the chamber 64 before the post 76 has engaged the piston 80. FIG. 4B shows the position of the post 76 and the piston 80 after the post 80 has entered the chamber 64 through receptacle 60. It can be seen there that the piston 80 is shifted radially outward thus shifting the reagent container 62 and causing it to open as described above.

Figure 5:
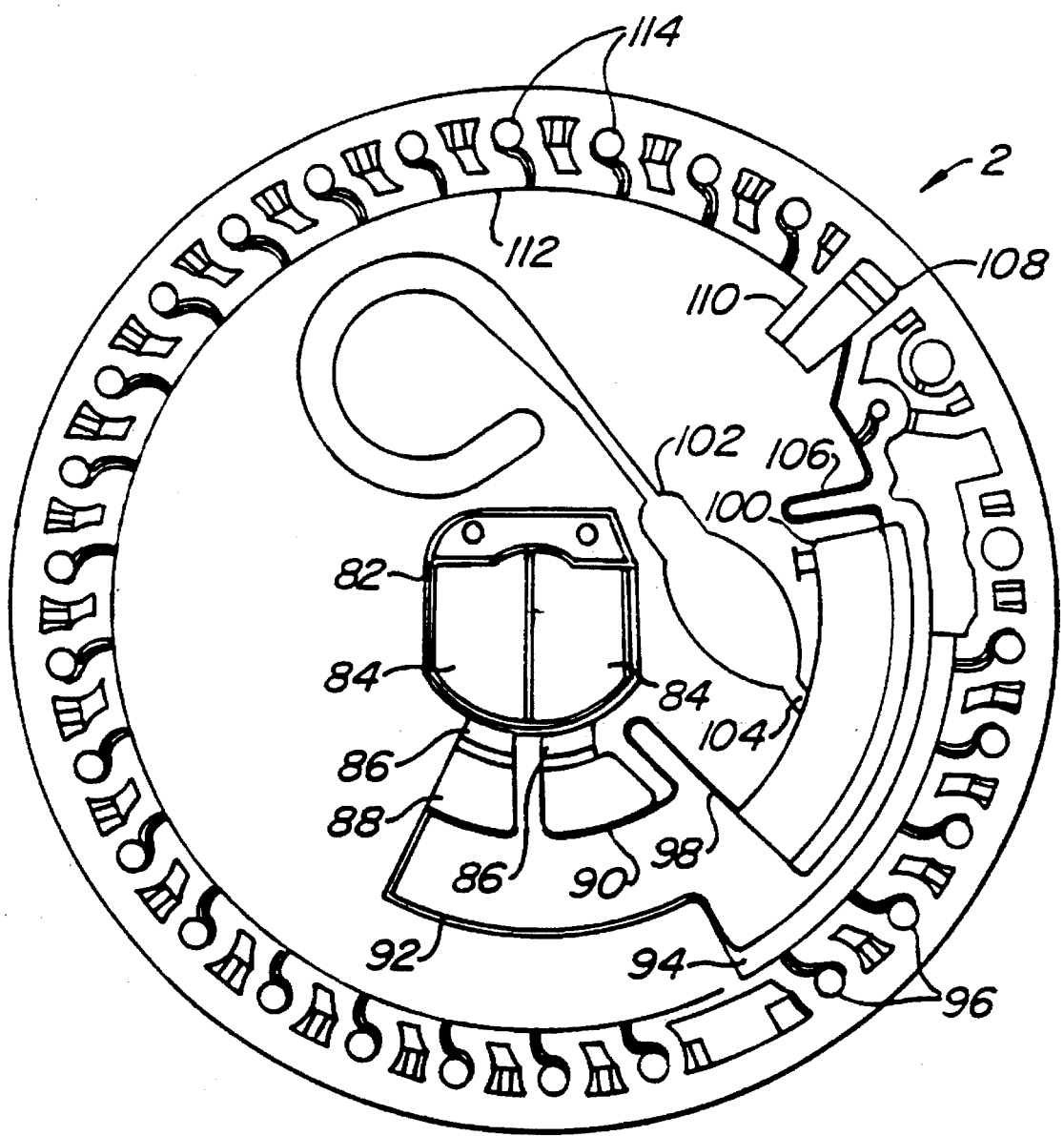
FIG. 5 is a top plan view of the bottom layer of a rotor of the present invention showing the position of the reagent container having two compartments in relation to various passages and chambers in the rotor.

FIG. 5 illustrates a rotor of the invention having a sealed reagent container 82 comprising more than one compartments 84. The chamber is positioned in the rotor body 2 and is opened in the same manner as described in the embodiment pictured in FIG. 1. For ease of description, the reagent container is shown without a foil seal, which is as described above. In this embodiment, each compartment 84 is radially inward from an outlet channel 86, each of which empties into a separate receiving chamber 88 and 90. The reagent container contains a diluent as described above. The reagent container 82 of this embodiment eliminates the need for a measuring chamber because each compartment 84 contains a predetermined volume of diluent which is used either as a control or for mixing with the biological sample.

After opening, the diluent in each compartment flows through the outlet channels 86 to the receiving chambers 88 and 90, which may contain marker compounds as described above. Diluent in receiving chamber 88 exits via passage 92 and enters collection chamber 94. The diluent then flows radially outward to system cuvettes 96 for use as a reference.

The predetermined volume of diluent in receiving chamber 90 exits through siphon 98 and enters the separation chamber 100, where it mixes with and dilutes the biological sample to be analyzed. The separation chamber 100 functions as described above. Whole blood is applied to the sample metering chamber 102 and metered as described above. The measured volume of blood then enters the separation chamber 100 through passage 104.

The diluted plasma exits the separation chamber 100 through siphon 106 and enters a second separation chamber 108 where further separation of cellular material is carried out. The diluted sample then exits through passage 110 and enters the collection chamber 112 where it is delivered to cuvettes 114 for optical analysis.

Although the foregoing invention has been described in detail for purposes of clarity of understanding, it will be obvious that certain modifications may be practiced within the scope of the appended claims. For instance, the receptacle which accepts the post may be positioned on surfaces other than the bottom surface of the rotor body. The post need not enter the receptacle as the rotor is mounted but may be moved mechanically at a preselected time during the testing cycle. In addition, the reagent container may contain reagents other than diluents, such as marker compounds, analytical reagents and the like.

What is claimed is:

1. A method of delivering a predetermined volume of liquid to a receiving chamber in an analytical rotor, the method comprising the steps of:

providing an analytical rotor having a top surface, a bottom surface, a container holding a liquid and having a seal, a receiving chamber disposed radially outward of the container, and means for holding the container against displacement;

inserting a post through a receptacle disposed on a surface of the rotor adjacent the container, thereby displacing the container and breaking the seal to release the liquid from the container; and spinning the rotor to effect the flow of the liquid into the receiving chamber.

2. The method of claim 1, wherein the post is disposed on a spindle in a centrifuge and the step of inserting the post through the receptacle is carried out by mounting the rotor on the spindle.

3. The method of claim 1, wherein the receptacle is disposed on the bottom surface of the rotor.

4. The method of claim 1, wherein the step of breaking the seal comprises peeling a laminated foil seal from the container.

5. The method of claim 1, wherein the step of breaking the seal comprises breaking open a rigid side on the container.

* * * * *